(12) United States Patent
Brands et al.

(10) Patent No.: US 7,411,088 B2
(45) Date of Patent: Aug. 12, 2008

(54) STEREOSELECTIVE SYNTHESIS OF A 4,4-DISUBSTITUTED CYCLOHEXANEPROPANOIC ACID

(75) Inventors: Karel Marie Joseph Brands, London (GB); Sarah Elizabeth Brewer, Biggleswade (GB); Antony John Davies, Princeton, NJ (US); Ulf H. Dolling, Westfield, NJ (US); Deborah Camille Hammond, Rickmansworth (GB); David Ross Lieberman, London (GB); Jeremy Peter Scott, Hertford (GB)

(73) Assignees: Merck & Co., Inc., Rahway, NJ (US); Merck Sharp & Dohme Ltd., Hoddesdon, Hertfordshire (GB)

( * ) Notice: Subject to any disclaimer, the term of this patent is extended or adjusted under 35 U.S.C. 154(b) by 0 days.

(21) Appl. No.: 10/589,098

(22) PCT Filed: Feb. 16, 2005

(86) PCT No.: PCT/GB2005/000544

§ 371 (c)(1), (2), (4) Date: May 14, 2007

(87) PCT Pub. No.: WO2005/080309

PCT Pub. Date: Sep. 1, 2005

(65) Prior Publication Data

US 2007/0225520 A1    Sep. 27, 2007

Related U.S. Application Data

(60) Provisional application No. 60/546,343, filed on Feb. 20, 2004.

(51) Int. Cl.
  *C07C 315/00*  (2006.01)
(52) U.S. Cl. .................... 562/429; 568/31
(58) Field of Classification Search .............. None
  See application file for complete search history.

(56) References Cited

U.S. PATENT DOCUMENTS

| | | | | |
|---|---|---|---|---|
| 6,984,663 | B2 * | 1/2006 | Churcher et al. | 514/570 |
| 7,101,895 | B2 * | 9/2006 | Churcher et al. | 514/317 |
| 7,276,637 | B2 * | 10/2007 | Brands et al. | 585/407 |
| 7,304,094 | B2 * | 12/2007 | Churcher et al. | 514/618 |
| 2003/0114496 | A1 * | 6/2003 | Churcher et al. | 514/344 |
| 2004/0116404 | A1 * | 6/2004 | Pineiro et al. | 514/210.01 |

FOREIGN PATENT DOCUMENTS

| | | |
|---|---|---|
| WO | WO 02/081435 | 10/2002 |
| WO | WO 03/018543 | 3/2003 |
| WO | WO 2004/013090 | 2/2004 |

* cited by examiner

*Primary Examiner*—Yvonne Eyler
*Assistant Examiner*—M Louisa Lao
(74) *Attorney, Agent, or Firm*—William Krovatin; Raynard Yurd

(57) ABSTRACT

There is provided stereoselective route to a compound of formula I:

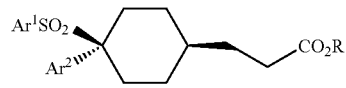

wherein R represents H or an alkali metal, $Ar^1$ represents 4-chlorophenyl and $Ar^2$ represents 2,5-difluorophenyl.

15 Claims, No Drawings

STEREOSELECTIVE SYNTHESIS OF A 4,4-DISUBSTITUTED CYCLOHEXANEPROPANOIC ACID

CROSS REFERENCE TO RELATED APPLICATIONS

This application is a U.S. National Phase application under 35 U.S.C. § 371 of PCT Application No. PCT/GB2004/000544, filed Feb. 16, 2005, which claims priority under 35 U.S.C. § 119(e) from U.S. provisional application Ser. No. 60/546,343, filed February 20, 2004.

This invention is in the field of synthetic organic chemistry, and in particular concerns a novel synthetic route to a particular class of 4,4-disubstituted cyclohexanepropanoic acids which have useful therapeutic properties, and which are intermediates in the synthesis of further compounds having therapeutic properties.

As disclosed in WO 03/018453, a particular class of cyclohexane derivatives have been found to have activity as inhibitors of the processing of amyloid precursor protein (APP) by γ-secretase into the β-amyloid peptide. Since the secretion of β-amyloid is believed to play a primary role in the onset and progression of Alzheimer's disease, the said cyclohexane derivatives are useful in the treatment and/or prevention of Alzheimer's disease.

Included within the aforementioned class of cyclohexane derivatives are cyclohexanepropanoic acids, and salts, esters and amides derived therefrom, in which the carbon atom in the 4-positon of the cyclohexyl ring is bonded to an aryl or heteroaryl group and also to an arylsulfonyl or heteroarylsulfonyl group. Said cyclohexanepropanoic acids exist in two stereoisomeric forms in which the propanoic acid group and the aryl- or heteroarylsulfonyl group are cis or trans with respect to the cyclohexane ring. Only the cis isomer has the requisite biological activity. The synthetic routes disclosed in WO 03/018453 and in US2003/0114496 involve condensation of a suitable 4,4-disubstituted cyclohexanone with an ylide and reduction of the resulting olefin. Isolation of the desired cis isomer requires the use of non-scaleable separation methods, or of expensive asymmetric reducing reagents and energy-intensive cryogenic conditions which render factory-scale preparations uneconomic.

There is therefore a need for an efficient, stereoselective synthesis of said cyclohexanepropanoic acids, amenable to execution on a large scale.

According to the invention there is provided a process for the preparation of a compound of formula I:

(1)

wherein R represents H or an alkali metal, $Ar^1$ represents 4-chlorophenyl and $Ar^2$ represents 2,5-difluorophenyl; comprising the steps of:

(a) stirring a mixture of a cis-sulfide of formula (2) and a trans-sulfide of formula (3):

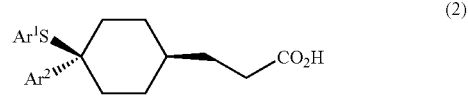

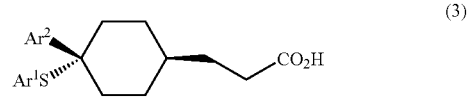

with 4-chlorobenzenethiol in an acidic medium in which said mixture of sulfides is partially soluble, causing preferential crystallisation of cis-sulfide of formula (2);

(b) collecting the cis-sulfide of formula (2);

(c) oxidising the cis-sulfide of formula (2) to the corresponding sulfone; and optionally (d) neutralising the product of step (c) with alkali.

Suitable identities for R include H, Na, K and Li, but R is preferably H or Na.

The key step in the process defined above is the isolation of a sulfide of formula (2) in which the sulfide group and the propanoic acid group are in the requisite cis configuration. Thereafter, the sulfide group may be oxidised to the required sulfone by conventional means, and (if desired) the propanoic acid functionality converted to the corresponding alkali metal salt such as the sodium salt by neutralisation with the appropriate alkali, or to a suitable ester or amide derivative as described in WO 03/018453.

It is surprisingly found that the cis-sulfide of formula (2) is significantly less soluble than its trans isomer (3) in a wide variety of solvents, and hence can crystallise preferentially from a mixture of the two isomers. Furthermore, the isomers are believed to interconvert under acidic conditions via an olefin of formula (4):

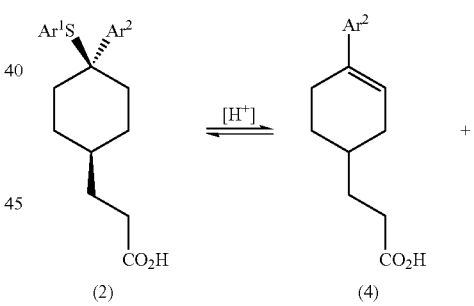

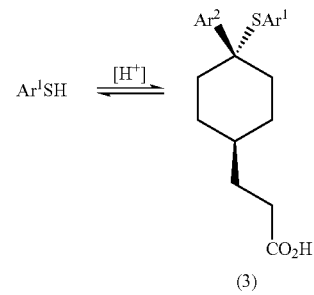

Hence, in accordance with step (a) of the above-defined process, when a mixture of sulfides (2) and (3) is stirred in an acidic medium in the presence of excess $Ar^1SH$ (i.e. 4-chlorobenzenethiol), essentially quantitative conversion of (3) to (2) may be achieved, with crystallisation of the latter in a high state of purity.

The nature and volume of the acidic medium must be such as to enable appreciable dissolution of the initial mixture of sulfides, otherwise the interconversion of the isomers becomes impractically slow (or non-existent). Generally speaking, increasing solubility of the sulfide mixture in the acidic medium leads to a higher rate of interconversion, but this may be at the expense of a reduced yield of crystalline product, with significant amounts of product remaining in solution. An initial solubility of about 0.1-1.0% w/v has been found to provide a suitable compromise, but values outside this range may be used if desired.

Addition of excess 4-chlorobenzenethiol to the system reduces the equilibrium concentration of the olefin (4) and hence increases the yield of sulfide (2). In at least some solvents, the presence of excess 4-chlorobenzenethiol also increases the solubility of the sulfides (2) and (3) and/or the solubility differential between the sulfides (2) and (3). The amount of excess 4-chlorobenzenethiol is not critical, but about 2-3 molar equivalents are typically used.

In one embodiment the acidic medium comprises a solvent and an acid. In principle, any solvent may be used in which a solubility differential exists in favour of the trans-sulfide (3). Examples include n-heptane, methylcyclohexane, trifluoroethanol, hexafluorobenzene, trifluorotoluene, hexafluoropropan-2-ol, acetonitrile and mixtures thereof. Others may be identified by simple experimentation. Particularly preferred solvents include hexafluoropropan-2-ol in admixture with another perfluorinated solvent such as perfluorohexane or perfluorinated 2-butyltetrahydrofuran (FC-75), e.g. a 1:1 v/v mixture of hexafluoropropan-2-ol and FC-75.

The acid is typically a strong organic acid such as a sulfonic acid or a perfluorinated carboxylic acid. Preferred acids include trifluoroacetic acid, benzenesulfonic acid, camphorsulfonic acid and $C_{1-4}$alkylsulfonic acids in which one or more of the carbon atoms may optionally be perfluorinated. Particularly preferred acids include is trifluoroacetic acid (TFA), trifluoromethanesulfonic acid (triflic acid) and methanesulfonic acid. (MSA). The quantity of acid present is typically about 10 mole % (based on the sulfide mixture) in the case of triflic acid, and typically about 25 mol % in the case of MSA. Larger quantities may be used if desired, but no particular advantage ensues.

In a second embodiment, the acidic medium consists primarily of the acid itself, if necessary diluted with water to adjust the solubility of the sulfides to a suitable level. A preferred acid for use in this embodiment is MSA, e.g. containing from about 5 to about 15% v/v water, preferably about 9 to about 11% v/v water.

The mixture of sulfides (2) and (3) is preferably stirred in the acidic medium for at least one hour, more preferably for at least 10 hours, such as overnight. Said stirring may be conducted at ambient or elevated temperatures. When hexafluoropropan-2-ol in admixture with another perfluorinated solvent is used as the acidic medium, overnight stirring at ambient temperature is suitable. When aqueous MSA solvent is used as the acidic medium, overnight stirring at about 35 to 45° C. is suitable.

After cooling (if necessary) the cis-sulfide of formula (2) is collected, e.g. by filtration. If desired, the filtrate may also be collected and recycled. This may be important when the acidic medium comprises one or more expensive fluorinated solvents. As an alternative to filtration, the cis-sulfide (2) may be collected by extraction into a solvent which is immiscible with the acidic medium. For example, when the acidic medium is aqueous MSA, extraction into ethyl acetate or isopropyl acetate may be used, the sulfide being isolated by subsequent evaporation of the extract to dryness. Prior to collecting the cis-sulfide, the mixture may be diluted with an antisolvent for the sulfide to promote further crystallisation of same. For example, when MSA containing 5-15% v/v water is used as the acidic medium, it is advantageous to dilute the medium with an approximately equal volume of water prior to collection of the cis-sulfide. The material thus obtained is typically more than 90% pure. If desired, further purification may be effected by recrystallisation (e.g. from acetonitrile or another solvent system) to provide cis-sulfide (2) that is essentially free from the trans isomer (3).

Step (c) of the process according to the invention, namely oxidation of the cis-sulfide (2) to the corresponding sulfone, may be effected by any of the oxidising agents conventionally used for the conversion of sulfides to sulfones, such as hydrogen peroxide, peroxyacetic acid or m-chloroperoxybenzoic acid (see, for example, Trost and Fleming, *Comprehensive Organic Synthesis*, 1993, Vol 7, 766). A preferred procedure comprises addition of about 3 equivalents of hydrogen peroxide to a solution of the sulfide in acetic acid, followed by heating at about 55-60° C. for about 5 hours, cooling to ambient temperature and dilution with water to precipitate the sulfone product.

Optional step (d) of the process according to the invention, namely neutralisation of the carboxylic acid group, may be carried out according to published procedures (e.g. US2003/0114496). A suitable process involves addition of 2M aqueous sodium hydroxide to a solution of the acid in propan-2-ol, followed by distillation of the solvent.

The mixture of cis- and trans-sulfides used in step (a) of the process of the invention may be generated by any suitable means. In one embodiment of the invention, said mixture is generated by the reaction of 4-chlorobenzenethiol with an olefin of formula (4):

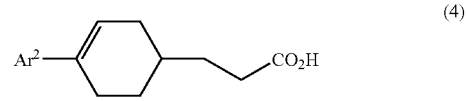

(4)

wherein $Ar^2$ represents 2,5-difluorophenyl. Advantageously, said reaction is carried out in the acidic medium subsequently used in step (a) of the process of the invention, so that the mixture of cis- and trans-sulfides is generated in situ.

In another embodiment of the invention, said mixture is generated by the reaction of 4-chlorobenzenethiol with a carbinol of formula (5):

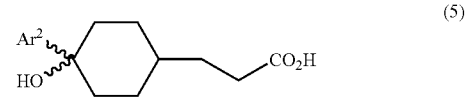

(5)

wherein Ar2 represents 2,5-difluorophenyl, said reaction being carried out in the presence of a Lewis acid, and the mixture of sulfides being isolated prior to carrying out step (a) of the process of the invention. In principle, any of the known Lewis acids may be used (e.g. those disclosed in "Lewis Acids in Organic Synthesis", ed. Yamamoto, pub. Wiley, 2000). Preferred examples include scandium triflate, boron trifluoride diethyl etherate, ethyl aluminium dichloride, zinc iodide, aluminium trichloride, tin tetrachloride, indium(II) chloride, indium(III) chloride, titanium tetrachloride, methyl aluminium dichloride and zinc triflate, of which boron trifluoride diethyl etherate is particularly preferred. The reaction may be carried out in an aprotic solvent such as dichloromethane or acetonitrile at reduced temperature (e.g. about −10 to −15° C.).

As will be readily apparent to those skilled in the art, carbinols represented by formula (5) exist as cis and trans isomers. Structural formula (5) encompasses both of said isomers, either as pure compounds or as mixtures in any proportion. Both isomers are equally useful in the invention, and carbinols (5) are typically generated and used as an approximately 1:1 mixture of cis and trans isomers.

In a preferred embodiment of the invention, said mixture of cis- and trans-sulfides is generated by the reaction of 4-chlorobenzenethiol with a carbinol mixture of formula (5) in the acidic medium subsequently used for step (a) of the process of the invention.

In a typical procedure in accordance with the invention, 4-chlorobenzenethiol is charged to a suitable reaction vessel and methanesulfonic acid added in sufficient quantity to dissolve most of the thiol when heated to about 40° C. (e.g. about 2.4 liters of acid per mole of thiol). Water (from about 8% to about 12% v/v with respect to the acid) is then added slowly with stirring and cooling so as to maintain a temperature of about 30-40° C. Thereafter, the carbinol (5) and/or olefin (4) (about 0.8-0.9 equivalents relative to the thiol) is added to the mixture. This results in rapid consumption of the carbinol and formation of a mixture comprising olefin (4) and cis-sulfide (2) together with its trans isomer. Aging of the above-described reaction mixture results in a selective accumulation of the desired cis-isomer, such that dilution with water, filtration and washing provides a high yield of crude product comprising >90% pure cis-sulfide (2). Reproducibility is facilitated by the addition of small amounts of pure cis-sulfide (2) as a seed prior to the aging step. Using this protocol, product of >99% purity is routinely obtainable via a single recrystallisation of the crude product. The quantity of seeding material is not critical, about 1% by weight relative to the carbinol (5) and/or olefin (4) being sufficient. Aging is carried out for at least 1 hour, preferably at least 3 hours and most preferably at least 10 hours (e.g. overnight). Aging can be conducted at ambient temperature but is preferably conducted by stirring at moderately elevated temperatures, for example in the range of about 35° C. to about 45° C.

At the end of the aging period, the mixture is cooled to ambient temperature and the crude product isolated, e.g. by dilution with water, filtration and washing of the crude solid product with further water. Alternatively, the diluted aqueous mixture can be extracted with a water immiscible organic solvent (e.g. ethyl acetate or isopropyl acetate) which is subsequently evaporated to dryness to provide the same crude product. The crude cis-sulfide (2) is preferably further purified by recrystallisation from a suitable solvent such as acetonitrile.

In further embodiments of the invention, the carbinol mixture of formula (5) is prepared by:

(a) conversion of carboxylic acid (6a) to magnesium salt (6b):

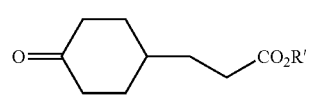

(a) R' = H
(b) R' = MgX (b) reaction of (6b) with $Ar^2$-M'; and
(c) treatment of the resulting product with acid;

wherein M' represents Li, MgX or $CeX_2$; X represents Cl, Br or I; and $Ar^2$ represents 2,5-difluorophenyl.

X preferably represents Cl. M' preferably represents Li.

Before reaction with $Ar^2$-M', the carboxylic acid (6a) is converted to the magnesium salt (6b), e.g. by treatment with one equivalent of $R^2MgX$, where $R^2$ represents $C_{1-6}$alkyl, preferably $C_{1-4}$alkyl such as methyl, ethyl, n-propyl or isopropyl (especially isopropyl), and X represents Cl, Br or I, preferably Cl. This process may be carried out in an ether solvent (preferably THF) at reduced temperature, e.g. below −60° C., under nitrogen or other inert gas. Alernatively, (6a) may be treated with solid $MgX_2$ in the presence of a base such as triethylamine, e.g. in THF.

The reagent $Ar^2$-M' may be prepared by conventional means. For example, treatment of $Ar^2$—H with a slight excess of n-butyllithium in the presence of one equivalent of N,N,N,N-tetramethylethylenediamine in THF below −60° C. under nitrogen provides a solution of $Ar^2$—Li suitable for use in the process (cf. Ong et al, *J. Med. Chem.* 1981, 24, 74 and Bridges et al, *J. Org. Chem.* 1990, 55, 773). Similarly, treatment of $Ar^2$—Br with one equivalent of $R^2MgX$ in THF below −10° C. under nitrogen provides a solution of $Ar^2$-MgX suitable for use in the process, where $R^2$ and X have the same definitions and preferred identities as before (cf. Abarbri et al, *Tetrahedron Lett.* 1999, 40, 7449). Addition of a THF solution of $Ar^2$-MgX to a slurry of $CeX_3$ in THF at about −10-0° C. provides a solution of $Ar^2$—$CeX_2$ suitable for use in the process.

Reaction of (6b) with $Ar^2$-M' is typically carried out in THF at about −60 to −20° C. (when M'=Li) or about −30 to −20° C. (when M'=MgX) or about 0° C. when M'=$CeX_2$. Conventional work-up (e.g. quenching with acetic acid at low temperature, warming to ambient, dilution with dilute hydrochloric acid and extraction into toluene) provides the crude carbinol mixture of formula (5) which may be further purified by recrystallisation (e.g. from a mixture of toluene and heptane).

The compound (6a) is known in the literature (Adkins et al, *J. Am. Chem. Soc.*, 1938, 60, 1467; and Adkins et al, *J. Am. Chem. Soc.*, 1940, 62, 2422). It is conveniently prepared by hydrogenation of 3-(4-hydroxyphenyl)propanoic acid or 3-(4-hydroxyphenyl)propenoic acid over Rh/$Al_2O_3$ in isopropyl acetate at about 70° C., followed by oxidation of the resulting cyclohexanol with NaOCl in the presence of $RuCl_3$ and acetic acid in isopropyl acetate. Details of these, and all other steps of the inventive process, are provided in the Examples section contained herein.

The compounds of formula (2), formula (4) and formula (5) are themselves novel, and individually constitute further aspects of the invention. The compounds of formula (4) are formed in situ when compounds of formula (5) are mixed with aqueous methanesulfonic acid and $Ar^1$—SH. However, they may be isolated in pure form if desired by treatment of carbinols (5) with acid (e.g. trifluoroacetic acid) in the absence of $Ar^1$—SH in an aprotic solvent such as dichloromethane.

The products of the novel process disclosed herein have an activity as inhibitors of the processing of APP by γ secretase, and are therefore useful in the treatment or prevention of disorders involving excessive secretion and/or deposition of β-amyloid, in particular Alzheimer's disease.

The products formed via the inventive process may be used to prepare pharmaceutical compositions comprising one or more of the said products or pharmaceutically acceptable salts thereof and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, such as the conventional tableting ingredients known to those skilled in the art, e.g. as described in WO 01/70677, and formed into unit dosage forms. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action, as described, for example, in WO 01/70677.

The liquid forms in which the compositions may be incorporated for administration orally or by injection include aqueous solutions, suitably flavoured syrups, aqueous or oil suspensions, and flavoured emulsions with edible oils, as described in WO 01/70677.

For treating or preventing Alzheimer's disease, a suitable dosage level of the active ingredient is about 0.01 to 250 mg/kg per day, preferably about 0.05 to 100 mg/kg per day, and especially about 0.1 to 50 mg/kg of body weight per day. The compounds may be administered on a regimen of 1 to 4 times per day. In some cases, however, dosage outside these limits may be used.

Assays for determining the level of activity of the relevant compounds towards γ-secretase are disclosed in WO 01/70677 and in *Biochemistry*, 2000, 39(30), 8698-8704. See also, *J. Neuroscience Methods*, 2000, 102, 61-68.

EXAMPLES

Example 1

3-(4-oxo-cyclohexyl)propanoic acid

A mixture of 3-(4-hydroxyphenyl)propenoic acid (3.33 Kg), 5% Rh/Al$_2$O$_3$ catalyst (248 g) and isopropyl acetate (IPAc) (30 L) was hydrogenated (200 psi) at 70° C. for 12 hours, then cooled and filtered.

To the resulting solution of 3-(4-hydroxycyclohexyl)propanoic acid was added RuCl$_3$ (42 g) and acetic acid (5.6 Kg). After cooling to 5° C., aqueous NaOCl (10-13%, 26 Kg) was added slowly with stirring, maintaining the temperature at 5° C. After stirring a further 3 hours at 5° C., 3N HCl (20 L) and IPAc (15 L) were added, the layers were separated and the aqueous layer extracted with IPAc (2×20 L). The combined organics were washed with 2M aqueous NaHSO$_3$ (10 L), dried (MgSO$_4$), treated with charcoal and filtered. The resulting solution was concentrated, and the solvent switched to heptane:IPAc 2:1 (20 L). This solution was seeded and the solvent switched to 9:1 heptane:IPAc, giving the product as a white solid which was collected, washed with heptane and dried under nitrogen.

Example 2 cis and trans-3-[4-(2,5-difluorophenyl)-4-hydroxycyclohexyl]propanoic acid

Method 1

N,N,N,N-tetramethylethylenediamine (8.8 ml, 57.8 mmol) was diluted with THF (70 mL) and purged with N$_2$ (3×) before cooling to −70° C. Butyllithium (25.2 mL, 57.8 mmol) was then added dropwise maintaining the temperature below −60° C. After aging 10 minutes at −65° C., 1,4-difluorobenzene (6 g, 5.4 mL, 52.6 mmol) was added dropwise, maintaining the temperature below −60° C., and the resulting solution was aged at −60° C. for 90 minutes.

In a separate vessel, 3-(4-oxo-cyclohexyl)propanoic acid (5.38 g, 31.6 mmol) in THF (80 mL) was purged with N$_2$ (3×) before cooling to −65° C. Isopropylmagnesium chloride (2M in THF) (15.5 mL, 31.0 mmol) was added dropwise over 30 min keeping the temperature below −60° C. The resultant solution was warmed to −10° C., then added slowly to the aryllithium solution prepared above, maintaining the temperature below −60° C. Upon complete addition, the temperature was allowed to warm to −20° C. slowly. The thick slurry was quenched by the dropwise addition of acetic acid (6 mL, 104 mmol) below 0° C. and allowed to warm to ambient. 2M HCl (140 mL) was charged to the reaction mixture followed by toluene (140 mL). The layers were cut and the organic layer was washed with H$_2$O (1×100 mL).

Evaporation in vacuo to dryness afforded ~13 g of crude product. This was redissolved in toluene (45 mL) at 80° C. then allowed to cool to 45° C. and seeded, at which point a seedbed formed. Heptane (45 mL) was added dropwise over 30 min at 45° C. then the slurry was allowed to cool to ambient. After 19 hours, the slurry was filtered, washed with 2:1 heptane:toluene (15 ml) then heptane (15 ml) and dried under vacuum at 50° C.

Method 2

1-Bromo-2,5-difluorobenzene (157.3 g, 0.815 mol) was diluted with THF (500 mL) and purged with N$_2$ (3×) before cooling to −30° C. Isopropylmagnesium chloride (2.0M in THF) (400 mL, 0.80 mol) was then added dropwise maintaining a temperature below −10° C. The resultant opaque solution of 2,5-difluorophenylmagnesium grignard was aged 1.0 hr at −10° C.

In a separate vessel, 3-(4-oxo-cyclohexyl)-propionic acid (85.1 g, 0.50 mol) in THF (1000 mL) was purged with N$_2$ (3×) before cooling to −58° C. Isopropylmagnesium chloride (2.0M in THF) (240 mL, 0.48 mol) was added dropwise maintaining a temperature below −55° C. The resultant solution was aged for 0.5 h at −55 to −50° C. then warmed to −30° C. over 15 min and held at this temperature a further 0.5 h. This solution was added slowly to the solution of difluorophenylmagnesium grignard cooled to −30° C., so that the temperature remained in the range −30 to −20° C. The resultant thick slurry was aged for 0.75 h below −10° C. The mixture was quenched with acetic acid (86 mL, 1.50 mol) below 5° C., warmed to 10° C., then treated with 1M HCl (750 mL) and toluene (750 mL), aged at 25° C. for 10 min and then the layers cut. The organic layer was washed with H$_2$O (1×1250 mL) and then extracted with 1M NaOH (1250 mL). The NaOH layer was stirred with toluene (1500 mL) before 2M HCl (700 mL) was charged at 22° C. and the mixture agitated for 5 min. The toluene layer was washed with H$_2$O (2×1000 mL) then filtered and evaporated in vacuo to dryness. The crude product was purified as described in method one.

Example 3 cis- and trans-3-[4-(4-chlorophenyl)thio-4-(2,5-difluorophenyl)cyclohexyl]propanoic acid 4-Chlorobenzenethiol (15.67 g, 108 mmol) in dichloromethane (46 ml) under nitrogen was cooled to −15° C. and treated with boron trifluoride diethyl etherate (14.3 g, 101 mmol). A solution of the carbinol mixture from Example 2 (22 g, 77 mmol) in dichloromethane (245 ml) was added slowly, keeping the temperature in the range between −9 and −15° C. After stirring a further two hours, the solvent was evaporated, replaced with acetonitrile, and this also evaporated. The residue was slurried with acetonitrile (30 ml) and water (100 ml) added. The resulting solid was filtered, washed with water, dried at 40° C. in vacuo and recrystallised from heptane. HPLC analysis indicated a 1:1 mixture of cis and trans isomers.

Example 4 cis -3-[4-(4-chlorophenyl)thio-4-(2,5-difluorophenyl)cyclohexyl]propanoic acid

The product from Example 2 (100 mg) and 4-chlorothiophenol (70 mg) were added to a mixture of hexafluoropropan-2-ol (0.5 ml) and FC-75 (0.5 ml), followed by triflic acid (8 μl). The resulting slurry was stirred overnight at ambient temperature, then filtered. HPLC analysis of the solid product indicated a mixture of 98.5% of the cis isomer and 1.5% of the trans isomer had been obtained.

Example 5 cis-3-[4-(4-chlorophenyl)thio-4-(2,5-difluorophenyl)cyclohexyl]propanoic acid

To a stirred mixture of 4-chlorothiophenol (65.0 g, 0.449 mol) and methanesulfonic acid (1.07 L) under nitrogen was slowly added water (118 ml), with cooling to maintain a temperature of 30-40° C. The carbinol from Example 2 (106.8 g, 0.374 mol) was added in a single portion, then after 10 minutes 1 g of purified cis-sulfide was added as seed. The mixture was stirred overnight at 36-42° C., cooled, and diluted slowly with water (1.07 L) with continued cooling to maintain a temperature of 22-39° C. After aging a further 30 minutes, the white solid was collected by filtration, washed with water and dried at 40° C. under vacuum. The crude product was slurried with acetonitrile (approximately 300 ml per 100 g of product), heated to reflux until dissolution was complete, then allowed to cool. The resulting crystalline material was collected, washed with further acetonitrile and dried 40° C. under vacuum. Final purity was assayed as 98.7 wt %.

Example 6 cis-3-[4-(4-chlorophenyl)sulfonyl-4-(2,5-difluorophenyl)cyclohexyl]propanoic acid The product from Example 5 (5.0 g, 12.17 mmol) in acetic acid (50 ml) was treated dropwise at 50° C. with hydrogen peroxide (27.5 wt %, 4.07 ml, 36.5 mmol) and the mixture kept at 55-60° C. for 4.75 hours. After cooling to ambient temperature, water (100 ml) was added dropwise and the resulting slurry stirred a further 1 hour. The product was collected by filtration, washed with water and dried at 40° C. in vacuo.

Example 7 cis-3-[4-(4-chlorophenyl)sulfonyl-4-(2,5-difluorophenyl)cyclohexyl]propanoic acid, sodium salt Product from Example 6 (10 g, 0.226 mol) in isopropanol (2 L) at 45° C. was treated with 2M aqueous sodium hydroxide (112 ml). The resulting solution was distilled at atmospheric pressure, removing 1 L distillate. Fresh isopropanol (1 L) was added and the distillation repeated. After adding further fresh isopropanol (1 L) and repeating the distillation again, the mixture was allowed to cool to ambient and aged a further 1 hour. The product was collected by filtration, washed with isopropanol and dried at 40° C. in vacuo.

Example 8

[4-(2,5-difluorophenyl)cyclohex-3-enyl]propanoic acid

Trifluoroacetic acid (6.8 ml, 87.9 mmol) was added to a solution of the product of Example 2 (2.5 g, 8.79 mmol) in dichloromethane (40 ml). The resulting mixture was stirred at ambient temperature overnight and then partitioned between water (50 ml) and IPAc (150 ml). The layers were separated. The organic layer was washed with water (50 ml) and brine (50 ml), dried ($Na_2SO_4$) and evaporated. The residue was recrystallised from IPAc, and dried at 40° C. in vacuo.

The invention claimed is:

1. A process for the preparation of a compound of formula (1):

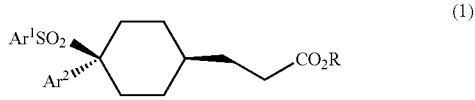

wherein R represents H or an alkali metal, $Ar^1$ represents 4-chlorophenyl and $Ar^2$ represents 2,5-difluorophenyl; comprising the steps of:
 (a) stirring a mixture of a cis-sulfide of formula (2) and a trans-sulfide of formula (3):

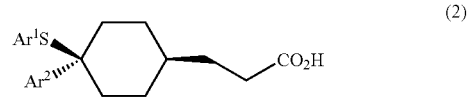

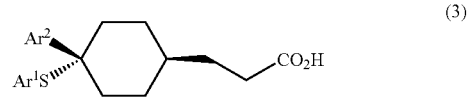

with 4-chlorobenzenethiol in an acidic medium in which said mixture of sulfides is partially soluble, causing preferential crystallisation of cis-sulfide of formula (2);
 (b) collecting the cis-sulfide of formula (2);
 (c) oxidising the cis-sulfide of formula (2) to the corresponding sulfone; and optionally
 (d) neutralising the product of step (c) with alkali.

2. A process according to claim 1 wherein said acidic medium comprises an acid selected from trifluoroacetic acid and $C_{1-4}$alkylsulfonic acids in which one or more of the carbon atoms may optionally be perfluorinated.

3. The process according to claim 2 wherein the acid is trifluoroacetic acid, trifluoromethanesulfonic acid or methanesulfonic acid.

4. A process according to claim 2 wherein said acidic medium additionally comprises a solvent selected from n-heptane, methylcyclohexane, trifluoroethanol, hexafluorobenzene, trifluorotoluene, hexafluoropropan-2-ol, acetonitrile and mixtures thereof.

5. A process according to claim 1 wherein the acidic medium is methanesulfonic acid containing from about 5 to about 15% water by volume.

6. A process according to claim 1 wherein the mixture of cis-sulfide of formula (2) and trans-sulfide of formula (3) is generated by reaction of 4-chlorobenzenethiol with an olefin of formula (4):

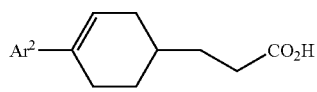
(4)

wherein Ar² represents 2,5-difluorophenyl, said reaction being carried out in the acidic medium used in step (a) of the said process.

7. A process according to claim 1 wherein the mixture of cis-sulfide of formula (2) and trans-sulfide of formula (3) is generated by reaction of 4-chlorobenzenethiol with a carbinol of formula (5):

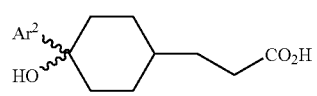
(5)

wherein Ar² represents 2,5-difluorophenyl, said reaction being carried out in the presence of a Lewis acid, and the mixture of sulfides being isolated prior to carrying out step (a) of the said process.

8. A process according to claim 1 wherein the mixture of cis-sulfide of formula (2) and trans-sulfide of formula (3) is generated by reaction of 4-chlorobenzenethiol with a carbinol of formula (5):

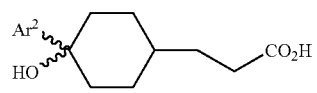
(5)

wherein Ar² represents 2,5-difluorophenyl, said reaction being carried out in the acidic medium used in step (a) of the said process.

9. A process according to claim 6 wherein the acidic medium comprises an acid and hexafluoropropan-2-ol together with a co-solvent selected from perfluorohexane and perfluorinated 2-butyltetrahydrofuran.

10. A process according to claim 9 wherein the acid is trifluoromethanesulfonic acid.

11. A process according to claim 6 wherein the acidic medium is methanesulfonic acid containing from about 5 to about 15% water by volume.

12. A process according to claim 7 wherein the carbinol of formula (5) is prepared by:
(a) conversion of carboxylic acid (6a) to magnesium salt (6b):

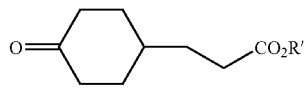
(6)

(a) R' = H
(b) R' = MgX (b) reaction of (6b) with Ar²-M'; and
(c) treatment of the resulting product with acid;
wherein M' represents Li, MgX or CeX₂;
X represents Cl, Br or I; and
Ar² represents 2,5-difluorophenyl.

13. The compound of formula (5):

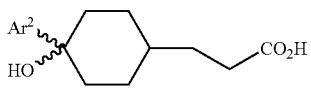
(5)

where Ar² is 2,5-difluorophenyl.

14. The compound of formula (4):

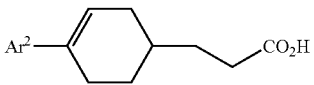
(4)

wherein Ar² is 2,5-difluorophenyl.

15. The compound of formula (2):

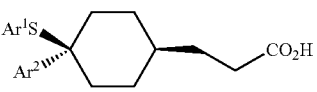
(2)

where Ar¹ is 4-chlorophenyl and Ar¹ is 2,5-difluorophenyl.

* * * * *